United States Patent [19]
Poll et al.

[11] Patent Number: 5,243,077
[45] Date of Patent: Sep. 7, 1993

[54] PROCESS FOR THE PREPARATION OF 4,4'-BIS-(4-AMINOPHENOXY)-DIPHENYL SULFONE

[75] Inventors: Günter Poll, Marl; Friedrich Sosna, Dorsten; Jürgen Finke, Marl, all of Fed. Rep. of Germany

[73] Assignee: Huels Aktiengesellschaft, Marl, Fed. Rep. of Germany

[21] Appl. No.: 790,308

[22] Filed: Nov. 12, 1991

[30] Foreign Application Priority Data

Nov. 12, 1990 [DE] Fed. Rep. of Germany ....... 4035882

[51] Int. Cl.$^5$ .......................................... C07C 213/06
[52] U.S. Cl. .................................................. 564/430
[58] Field of Search ...................... 564/405, 430, 440

[56] References Cited

U.S. PATENT DOCUMENTS 3,817,921 6/1974 Brode et al. .......................... 564/430
4,754,068 6/1988 Yamaguchi et al. ................. 564/430

Primary Examiner—Glennon H. Hollrah
Assistant Examiner—Brian M. Burn
Attorney, Agent, or Firm—Millen, White, Zelano & Branigan

[57] ABSTRACT 4,4'-bis-(4-aminophenoxy)-diphenyl sulfone (BAPS) has been prepared from 4-aminophenol and a 4,4'-dihalodiphenyl sulfone in an organic solvent in the presence of an inorganic carbonate in a one-stage reaction, a pure product having a high melting point being obtained.

15 Claims, No Drawings

PROCESS FOR THE PREPARATION OF 4,4'-BIS-(4-AMINOPHENOXY)-DIPHENYL SULFONE

BACKGROUND OF THE INVENTION

The invention relates to a novel process for the preparation of 4,4'-bis-(4-aminophenoxy)-diphenyl sulfone from 4-aminophenol and 4,4'-dihalodiphenyl sulfone in an organic solvent.

4,4'-bis-(4-aminophenoxy)-diphenyl sulfone (BAPS) is an important monomer for the preparation of high-melting polyamides, polyimides, and polyamidoimides. It is also suitable as a curing agent for epoxides.

According to DE-A-19 09 520, BAPS is prepared from p-aminophenol, sodium hydroxide solution, or potassium hydroxide solution and a 4,4'-dihalodiphenyl sulfone in an organic solvent. This is a two-stage process. First, the p-aminophenolate is prepared and the water formed is distilled off. BAPS is then obtained by the reaction of p-aminophenolate with 4,4'-dichlorodiphenyl sulfone. The product is precipitated with water, dissolved, treated with active carbon and reprecipitated. It then has a melting point of 191°–192° C., which can be increased to 193°–194° C. by recrystallization.

According to DE-A-23 15 607 (U.S. Pat. No. 3,817,921), BAPS is prepared from p-aminophenol, sodium hydroxide solution, and 4,4'-dichlorodiphenyl sulfone, stoichiometric amounts of the starting compounds being used. This is also a two-stage process. In the first stage, water is distilled off with the aid of the entraining agent chlorobenzene. After precipitation twice, a product having a melting point of 177°–187° C. is obtained. After recrysallization, the melting point is 188°–191° C.

Furthermore, according to Kawakami et al. [*Journal of Polymer Science, Polymer Chemistry Edition*, Vol. 12 (1974), 565–573], BApS is prepared from p-aminophenol, sodium hydroxide, and 4,4'-dichlorodiphenyl sulfone in dimethyl sulfoxide. A product having a melting point of 189°–191° C. is obtained. After recrystallization, the melting point is 191°–192° C.

For polycondensation purposes, a BAPS which is as pure as possible and has as high a melting point as possible is required. BAPS having a melting point of less than 191° C. is still unsuitable, whereas a product having a melting point of 191°–193° C. merely leads to low-quality polycondensates having a dark color and poor mechanical properties. Accordingly, the known processes give a BAPS which is suitable or of limited use for polycondensations only after several purification steps and after recrystallization.

SUMMARY OF THE INVENTION

An object of the present invention was to develop a simplified process for the preparation of BAPS of high purity. An intention was as far as possible to obtain, after the end of the reaction, a product which is suitable for polycondensation purposes, even without recrystallization.

Upon further study of the specification and appended claims, further objects and advantages of this invention will become apparent to those skilled in the art.

According to the invention, these objects are achieved by carrying out the reaction in one stage and in the presence of an inorganic carbonate family compound.

For the purpose of the invention, one-stage reactions are reactions in which intermediates are neither isolated nor conveyed. It is possible, for example, to adopt a procedure here in which 4-aminophenol; 4,4'-dihalodiphenyl sulfone; and inorganic carbonate are mixed and then heated to the reaction temperature. It is also possible to heat 4-aminophenol and 4,4'-dihalodiphenyl sulfone and then to start the reaction by adding an inorganic carbonate.

The reaction is preferably carried out at 100°–250° C., temperatures of 120°–200° C. being particularly preferred. If the reaction temperature is above the boiling point of the solvent used, the reaction is carried out in a suitable pressure apparatus.

The reaction time is usually in the range of from 1 to 200 hours. Reaction times of 1–100 hours are preferred.

The reaction of 4-aminophenol and 4,4'-dihalodiphenyl sulfone can be carried out in compatible organic solvents such as ethers or in aliphatic halohydrocarbons. However, polar aprotic solvents are preferably used. Such solvents are, for example, dimethyl sulfoxide (DMSO); N-methylpyrrolidne (NMP); N-methylcaprolactam; N,N-dimethylformamide (DMF); N,N-dimethylacetamide (DMA); diphenyl sulfone; tetramethylene sulfone; chlorobenzene; or mixtures of these solvents.

The reaction is preferably carried out in DMSO or in NMP. The amount of solvent is such that the solids content during the reaction is 10–80%, preferably 20–70%.

Suitable inorganic carbonate family compounds are primarily carbonates and bicarbonates. For example, alkali metal and alkaline earth metal carbonates, such as lithium carbonate, sodium carbonate, potassium carbonate, magnesium carbonate, or calcium carbonate, can be used. The corresponding bicarbonates can likewise be employed. Zinc carbonate, basic zinc hydroxide carbonate, and other basic carbonates are also suitable. However, alkali metal carbonates are also preferably used. Sodium carbonate and potassium carbonate are very particularly preferred.

Particularly suitable 4,4'-dihalodiphenyl sulfones are the difluoro, the dichloro, and the dibromo compounds and the bromochloro, the bromofluoro, and the chlorofluoro compounds. 4,4'-dichlorodiphenyl sulfone is preferably used.

The molar ratio of 4,4'-dihalodiphenyl sulfone to 4-aminophenol is preferably in the range of from 1:2 to 1:3. A molar ratio of 1:2.01 to 1:2.4 is particularly preferred.

4,4'-dihalodiphenyl sulfone and inorganic carbonate are generally used in a molar ratio of 1:1 to 1:20. If the inorganic carbonate used is an alkali metal carbonate, the molar ratio is preferably 1:1 to 1:10. In the specific case where 4,4'-dichlorodiphenyl sulfone and an alkali metal carbonate are used, the molar ratio is preferably in the range of from 1:1 to 1:5.

A pure BAPS having a high melting point of, in general, more than 194° C. is obtained by the process according to the invention in a one-stage reaction procedure which is not technically complicated. The product can also be used directly for polycondensations, without recrystallization. The purity of the product of this invention can be readily determined conventionally using the DSC method; see, e.g., E. A. Turi, Thermal Characterization of Polymeric Materials, Academic Press, 1981, 208 ff; and W. F. Hemminger, H. K. Cammenga, Methoden der thermischen Analyse [Methods of Thermal Analysis], Springer-Verlag, 1989, 269 ff.

In the examples which follow, the procedure generally used is one in which the 4,4'-dihalodiphenyl sulfone, 4-aminophenol, and the inorganic carbonate are mixed in an organic solvent and the mixture is then heated to the reaction temperature. After the reaction, the mixture is cooled, after which BAPS is precipitated with the aid of a methanol/water mixture.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents, and publications, cited above and below, and of corresponding German Application P 40 35 882.8, filed Nov. 12, 1990, are hereby incorporated by reference.

EXAMPLES

Example 1

All work is carried out while blanketing with nitrogen.

50.25 g (0.175 mol) of 4,4'-dichlorodiphenyl sulfone, 40.11 g (0.368 mol) of 4-aminophenol and 55.10 g (0.193 mol) of $Na_2CO_3 \cdot 10\ H_2O$ in 200 ml of NMP are placed, at room temperature, in a 1 l three-necked flask having a stirrer, a reflux condenser and a nitrogen inlet tube. This mixture is heated to 180° C. in the course of one hour and then kept at 180° C. for 15 hours. The temperature is then reduced to 60° C. 500 ml of methanol/water mixture (1:1) are added. The BAPS formed is precipitated. The product is washed with methanol/water mixture and then dried.
Yield: 64.8 g (86% of theory)
$T_m$: 195.0° C. (according to DSC)
DSC determination of purity: 99.1 mol % of BAPS

Examples 2-10

The procedure is as in Example 1. However, the changes stated in Table 1 are made.

invention and, without departing from the spirit and scope thereof, can make various changes and modifications of the invention to adapt it to various usages and conditions.

What is claimed is:

1. A process for the preparation of 4,4'-bis-(4-aminophenoxy)-diphenyl sulfone comprising reacting 4-aminophenol and a 4,4'-dihalodiphenyl sulfone in an organic solvent, wherein the reaction is carried out in one stage in the presence of an inorganic carbonate, bicarbonate, or basic carbonate.

2. A process according to claim 1, wherein said reaction is carried out at from 100°-250° C.

3. A process according to claim 1, wherein said solvent is a polar, aprotic solvent.

4. A process according to claim 3, wherein said solvent is dimethyl sulfoxide or N-methylpyrrolidone.

5. A process according to claim 1, wherein said inorganic carbonate is an alkali metal carbonate.

6. A process according to claim 1, wherein said 4,4'-dihalodiphenyl sulfone is 4,4'-dichlorodiphenyl sulfone.

7. A process according to claim 1, wherein said 4,4'-dihalodiphenyl sulfone and 4-aminophenol are reacted in a molar ratio of 1:2 to 1:3.

8. A process accoridng to claim 7, wherein said molar ratio of 4,4'-dihalodiphenyl sulfone to 4- aminophenol is 1:2.01 to 1:2.4.

9. A process according to claim 1, wherein said 4,4'-dihalodiphenyl sulfone and inorganic carbonate are used in a molar ratio of 1:1 to 1:20.

10. A process according to claim 9, wherein said 4,4'-dihalodiphenyl sulfone and alkali metal carbonate are used in a molar ratio of 1:1 to 1:10.

11. A process according to claim 1, wherein the resultant product has a.melting point of greater than 194° C.

12. A process of claim 1, wherein said inorganic carbonate, bicarbonate, or basic carbonate has as cation an alkali metal, an alkaline earth metal, or zinc.

13. A process for the preparation of 4,4'-bis-(4-aminophenoxy)-diphenyl sulfone suitable for polycondensation purposes comprising reacting 4-aminophenol and a 4,4'-dihalodiphenyl sulfone in an organic solvent, wherein the reaction is carried out in one stage in the presence of an inorganic carbonate, bicarbonate, or basic carbonate and without subsequent recrystallization.

14. A process of claim 1, wherein said product sulfone is not subjected to subsequent recrystallization

TABLE 1

| Example | DCDPS[1] (mol) | p-Aminophenol (mol) | Inorg. carbonate | (mol) | Solvent | Reaction Time (h) | Reaction Temp. (°C.) | Yield (g) | Yield (%) | $T_m$ (°C.) | DSC Determination of purity (mol %) |
|---|---|---|---|---|---|---|---|---|---|---|---|
| 2 | 0.175 | 0.375 | $Na_2CO_3$ | 0.35 | NMP | 15 | 170 | 61.9 | 82 | 194.8 | 98.5 |
| 3 | 0.175 | 0.375 | $NaHCO_3$ | 0.4 | NMP | 24 | 180 | 60.8 | 81 | 194.3 | 97.4 |
| 4 | 0.175 | 0.40 | $Na_2CO_3$ | 0.20 | DMSO | 24 | 170 | 58.0 | 77 | 194.1 | 96.4 |
| 5 | 0.175 | 0.375 | $MgCO_3$ | 0.20 | NMP | 15 | 180 | 60.5 | 81 | 194.6 | 97.7 |
| 6 | 0.175 | 0.375 | $CaCO_3$ | 0.20 | NMP | 15 | 180 | 58.9 | 78 | 194.8 | 98.3 |
| 7 | 0.175 | 0.525 | $Na_2CO_3$ | 0.25 | NMP | 15 | 180 | 63.4 | 84 | 195.2 | 99.2 |
| 8 | 0.175 | 0.375 | $K_2CO_3$ | 0.20 | NMP | 6 | 170 | 65.6 | 87 | 194.7 | 98.3 |
| 9 | 0.175 | 0.375 | $K_2CO_3$ | 0.25 | NMP | 8 | 160 | 67.2 | 89 | 195.2 | 99.4 |
| 10 | 0.175 | 0.375 | $K_2CO_3$ | 0.35 | NMP | 8 | 160 | 63.4 | 84 | 195.1 | 99.2 |

[1]DCDPS: 4,4'-Dichlorodiphenyl sulphone

The preceding examples can be repeated with similar success by substituting the generically or specifically described reactants and/or operating conditions of this invention for those used in the preceding examples.

From the foregoing description, one skilled in the art can easily ascertain the essential characteristics of this prior to polymerization.

15. A process according to claim 1, wherein the product sulfone is not subjected to subsequent polymerization.

* * * * *